United States Patent [19]

Rancurel et al.

[11] 4,196,217

[45] Apr. 1, 1980

[54] HYDROXYLATED AMINES WITH BACTERIOSTATIC ACTIVITY

[75] Inventors: Alain Rancurel, Chartres; Georges Grenier, Epernon, both of France

[73] Assignee: Laboratoires Pharmascience, Courbevoie, France

[21] Appl. No.: 915,610

[22] Filed: Jun. 15, 1978

Related U.S. Application Data

[63] Continuation of Ser. No. 658,246, Feb. 17, 1976, abandoned.

[51] Int. Cl.$^2$ .................. A61K 31/205; A61K 31/21; A61K 31/13; A61K 31/14
[52] U.S. Cl. .................. 424/316; 260/584 R; 260/584 C; 424/298; 424/325; 424/329
[58] Field of Search ............ 260/584 R, 584 C, 501.1, 260/567.6 M, 583 P, 584 B; 424/316, 325

[56] References Cited

U.S. PATENT DOCUMENTS

| | | | |
|---|---|---|---|
| 2,246,524 | 6/1941 | Kyrides | 424/325 X |
| 2,548,679 | 4/1951 | Olin | 260/567.6 |
| 2,933,529 | 4/1960 | Hwa | 260/567.6 |
| 3,291,683 | 12/1966 | Lamb | 260/584 C X |
| 3,457,313 | 7/1969 | Baker | 260/584 R |
| 3,636,114 | 1/1972 | Tobler et al. | 260/567.6 |
| 3,879,464 | 4/1975 | Kalopissis et al. | 260/584 C |
| 4,087,550 | 5/1978 | Bouillon et al. | 424/325 X |

FOREIGN PATENT DOCUMENTS

| | | | |
|---|---|---|---|
| 636129 | 10/1963 | Belgium | 260/584 R |

OTHER PUBLICATIONS

Schlesier, "Chem. Ab.", vol. 58, Ab. No. 1148g (1963).
Ponomarev, "Chem. Ab."; vol. 48, Ab. No. 108h, (1954).
Sidgwick, "The Org. Chem. of Nitrogen", pp. 96–97 (1966).
Rose et al., "The Condensed Chem. Dict.", p. 477 (1956).
Ponomarev, "Chem. Ab.", vol. 48, Ab. No. 7548g (1954).
Gurova, "Chem. Ab.", vol. 75, Ab. No. 44187u (1971).

*Primary Examiner*—John Doll
*Attorney, Agent, or Firm*—Maky, Renner, Otto & Boisselle

[57] ABSTRACT

The invention relates to new chemical compounds and to processes for their preparation.

The compounds according to the invention correspond to the formula

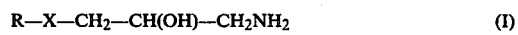

$$R-X-CH_2-CH(OH)-CH_2NH_2 \qquad (I)$$

in which
R is a saturated or unsaturated straight-chain $C_5$ to $C_{18}$ aliphatic radical and X represents —O—, —S—, —NH— or —CH$_2$—,
the salts, esters and quaternary alkyl ammonium salts of these compounds.

These compounds may be used in particular as medicaments, as antiseptics, sterilizing agents and preservatives.

5 Claims, No Drawings

HYDROXYLATED AMINES WITH BACTERIOSTATIC ACTIVITY

This is a continuation of application Ser. No. 658,246, filed Feb. 17, 1976, now abandoned.

This invention relates to new chemical compounds, to processes for their preparation and to the use of these compounds as sterilising agents and preservatives, especially in the cosmetics industry, and as antiseptics for example in dermatology.

SUMMARY OF THE INVENTION

The compounds according to the present invention have the following formula:

$$R-X-CH_2-CH(OH)-CH_2NH_2 \qquad (I)$$

in which
R represents a saturated or ethylenically or acetylenically unsaturated straight-chain $C_5$-$C_{18}$ aliphatic radical and X represents —O—, —S—, —NH— or $CH_2$—, preferably an oxygen or sulphur atom.

The present invention also relates to the salts and esters of these compounds, more especially their hydrochlorides, hydrobromides and acetates, and also to their alkylated quaternary ammonium derivatives.

The nonyl, decyl and dodecyl radicals are mentioned in particular as examples of the saturated aliphatic radical which may be represented by the radical R.

More particularly, the present invention relates to compounds corresponding to the formula:

$$R_1-X_1-CH_2-CH(OH)-CH_2NH_2 \qquad (Ia)$$

in which
$R_1$ is an unbranched $C_5$ to $C_{14}$ alkyl chain and $X_1$ is —O— or —S—, and even more particularly to the compound of formula Ia in which $R_1$ is the decyl radical and $X_1$ is oxygen, i.e. 3-decyloxy-2-hydroxy-1-aminopropane in the form of its hydrochloride, hydrobromide or acetate.

The compounds according to the invention and in particular the compounds corresponding to formula Ia may be prepared by processes similar to those used for preparing the lower homologues (cf. in particular: Chem. Abs. 1953, 47, 101i; 1954, 48, 108i; 1954, 48, 7549b; 1955, 49, 10850g; 1956, 50, 10700f; 1965, 62, 16783e; and 1971, 75, 44187u).

However, the compounds of formula (I), in which X is oxygen or sulphur, are preferably prepared by the following process:

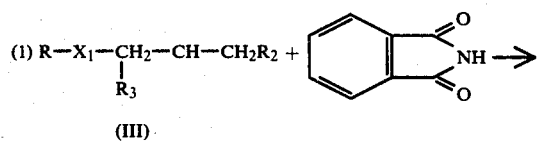

(III)

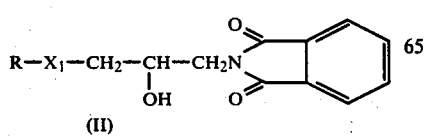

(II)

(II)

$$NH_2-NH_2 \longrightarrow R-X_1-CH_2-CH-CH_2NH_2 +$$
$$\phantom{NH_2-NH_2 \longrightarrow R-X_1-CH_2-}\overset{|}{OH}$$

(I)

In these formulae, $X_1$ represents —O— or —S—, R has the same meaning as in formula (I) and $R_3$ and $R_2$ together represent an epoxy radical or $R_3$ represents a hydroxy radical and $R_2$ a halogen atom, preferably chlorine or bromine.

The reaction (1) is carried out in the presence of a compound, such as potassium or sodium carbonate, which is capable of making the phthalimide react in the form of its sodium or potassium derivative.

The hydrolysis reaction (2) is carried out in the presence of hydrochloric acid.

The compound of formula (III) may be prepared for example by reacting an epihalohydrin:

with an alcohol in the presence of a catalyst, such as stanic chloric, zinc chloride, ferric chloride, the boron fluoetherate complex or tosylic acid. The product obtained is a halogenated alcohol.

The epoxide of formula (III) may be prepared by cyclizing the above halogenated alcohol or by other known methods.

The compounds (I) according to the invention may also be prepared by reacting ammonia or an amine with a halogenated alcohol of formula (III) or with an epoxide of formula (III). However, these reactions generally result in the formation of a mixture of amines. The bromine derivatives are more suitable than the other halogen derivatives for obtaining primary amines, but unfortunately they are more expensive. Derivatives of the alkanolamine type are preferably obtained by reducing the corresponding cyanhydrin with a compound of the lithium aluminium hydride type. The compounds according to the invention are then separated from the reaction mixture and purified by known methods, such as liquid-liquid extraction or fractional crystallisation.

DESCRIPTION OF PREFERRED EMBODIMENTS

The preparation of the compounds according to the invention is illustrated by, but by no means limited to, the following Examples.

EXAMPLE 1

Preparation of 3-decyloxy-2-hydroxy-1-aminopropane 300 cc of decanol, 90 cc (106 g) of freshly distilled epichlorhydrin and 1.5 g of anhydrous ferric chloride are introduced into a 1 liter flask.

After the reaction mixture has been heated at 145° C. for 10 hours, the 2-decyloxy-1-chloromethyl ethanol is distilled, first in a water jet vacuum and then in a vane-pump vacuum.

B.P. of the chlorine derivative at 0.06 mm: 128°–130° C.

yield: 65%

20 g of the chlorine derivative and a finely powdered mixture of 14.8 g of phthalimide and 8.4 g of potassium carbonate are introduced into a reactor equipped with a mechanical stirrer.

This mixture is heated under reflux for 5 hours at 190° C. in an oil bath. After removal of the heat, 100 cc of hot ethanol are introduced and the mixture filtered to eliminate the potassium chloride which has formed.

The ethanolic solution obtained is treated while stirring with a magnetic stirrer, with 5 cc of 98% hydrate hydrazine, for 30 minutes at ambient temperature and then for 2 hours under reflux. An insoluble precipitate is formed. This mixture is then acidified with hydrochloric acid and refluxed for 15 minutes. After cooling and filtration, the solution obtained is evaporated in vacuo.

The evaporation residue is taken up in 50 cc of water and, after standing in a refrigerator for 3 hours, the solution is filtered.

The filtrate is treated with a 10% soda solution until a basic pH is obtained. The 3-decyloxy-2-hydroxy-1-aminopropane is then extracted with ether, the ether phase is washed and dried over anhydrous sodium sulphate and filtered.

A stream of hydrochloric acid is introduced into the ethereal solution and, after standing in a refrigerator, the product is centrifuged to obtain crystals of 3-decyloxy-2-hydroxy-1-aminopropane.

The compound obtained is soluble in water and begins to melt at a temperature of 60° C.

EXAMPLES 2 TO 5

The procedure is as in Example 1 except that the decanol is replaced by the alcohol or thiol indicated. The following compounds are obtained:

myristic alcohol gives 3-tetradecyloxy-2-hydroxyamino-1-propane hydrochloride (the corresponding chlorinated alcohol distills at 160°–180° C./0.5 mm Hg) which has a melting point of 65° C. (softening), is soluble in water, and possesses the following elemental analysis:

calculated: H 11.74; C 63.06; N 4.32; Cl 10.97, observed: H 11.88; C—; N 4.54; Cl 10.86.

n-octadecyl alcohol gives 3-octadecyloxy-2-hydroxy-1-aminopropane hydrochloride, which is soluble in water;

ethanol gives 3-ethoxy-2-hydroxy-1-aminopropane hydrochloride decane thiol gives 3-decanethio-2-hydroxy-1-aminopropane hydrochloride which has a melting point of 270° C., is soluble in alcohol, and has the following elemental analysis:

calculated: C 55.02; H 10.58; N 4.94; Cl 12.52; S 11.29
observed: C 53.47; H 10.10; N 5.3; Cl 15.71; S 10.05.

EXAMPLE 6

Preparation of 3-dodecyloxy-2-hydroxy-1-aminopropane hydrochloride

By replacing the 3-decyloxy-2-hydroxy-1-chloropropane (compound III) used in Example 1 by 3-dodecyloxy-1,2-epoxy propane, 3-dodecyloxy-2-hydroxy-1-aminopropane is obtained in the form of its hydrochloride: melting point: 60° C. (softening).

EXAMPLE 7

Preparation of 3-decyloxy-2-hydroxy-N,N,N-trimethyl-1-ammonium chloride

A mixture of 15 g of 3-decyloxy-1-chloro-2-propanol prepared in accordance with Example 1, 20 cc of trimethylamine and 20 cc of benzene is heated for 6 hours at 120° C. in an autoclave.

After cooling and treatment with ether, the mixture precipitates a product which is centrifuged. 8.4 g of the title compound are obtained by recrystallisation in acetone. It has a melting point of 88° C., is soluble in water, and has an elemental analysis as follows:

calculated: C 62.03; H 11.63; N 4.52; Cl 11.47, observed: C 63.20; H 11.68; N 4.49; Cl 11.32.

EXAMPLE 8

Preparation of 3-decyloxy-2-hydroxy-1-aminopropane hydrobromide

A methanolic solution of 28.7 g of 3-decyloxy-2-hydroxy-1-bromopropane (prepared in accordance with Example 1 from epibromhydrin) and excess ammonia is heated for 24 hours 120° C. in an autoclave.

After the reaction produce has been evaporated to dryness and taken up in ether, the title product is obtained in a yield of 22.3 g: melting point: 120° C. (softening at 60° C.). The product is soluble in water, and has an analysis of:

M.theoretical: 312.3
argentimetry: 306.5
nitrogen: 310.9

EXAMPLE 9

Preparation of 3-octyloxy-2-hydroxy-1-aminopropane hydrochloride

The procedure is as in Example 8 using as starting product 3-octyloxy-2-hydroxy-1-bromopropane (prepared in accordance with Example 1 from epibromohydrin and octanol).

The hydrobromide obtained is passed through a column of ion exchange resin (CG-400-Cl) so as to obtain the corresponding hydrochloride. The title compound is obtained after recrystallisation from acetone and has the following properties:

melting point: 55° C. (softening), soluble in water,
elemental analysis: calculated: Cl 14.80; N 5.84; observed: Cl 14.88; N 5.95.

EXAMPLE 10

Preparation of 3-dodecyloxy-2-hydroxy-1-aminopropane hydrochloride

A methanolic solution containing 10 g of 3-dodecyloxy-1,2-epoxy propane and an excess of ammonia is heated for 4 hours at 100° C. in an autoclave. After cooling, evaporation, treatment with ether, filtration and treatment with gaseous hydrochloric acid, a product is obtained which, after recrystallisation from methyl ethyl ketone, gives 4.65 g of the title compound.

EXAMPLES 11 AND 12

The reduction in ether in the presence of lithium aluminium hydride of the cyanhydrin of decanal, followed by recrystallisation from a mixture of isopropyl ether and methanol, gives 2-hydroxy-1-aminodecane.

2-hydroxy-1-amino tridecane is obtained from lauric aldehyde by the same process.

The present invention also relates to the use of compounds of formula (I) and more particularly of formula (Ia) as sterilising agents and/or preservatives.

The compounds according to this invention have a wide range of activity against microorganisms, i.e. not only bacteria, fungi and yeasts, but also bacterial spores.

Their wide range of activity, their very low toxicity and the fact that they do not attach the skin, or mucosa nor are corrosive to metals, makes them suitable for use as sterilising agents and preservatives, especially in cosmetology and surgery.

However, the compounds according to the invention are antiseptic medicaments intended in particular for the treatment and prevention of disorders caused by gram-negative bacteria, in human or veterinary medicine.

The compounds may be used either on their own or in admixture, in particular with other bactericides, in order to widen the range of activity of the compositions obtained.

By virtue of their outstanding solubility in water, the compounds according to the invention are preferably used in the form of aqueous solutions, although they may also be packaged in other forms, such as pastes (soaps for example), creams, soluble granules, powders, alcoholic solutions, according to the particular application for which they are intended. For example, the liquid formulations will be particularly suitable for the sterilisation of instruments or apparatus.

The studies reported below were carried out in particular with 3-decyloxy-2-hydroxy-1-aminopropane hydrochloride which will be referred to hereinafter as "compound 1."

Toxicity

The acute toxicity of compound 1 was determined by intragastric administration to male rats of the Wister AF-EOPS strain weighing from 120 to 130 g, and to male mice of the NMRI-Han strain weighing between 22 and 25 g and aged about 6 weeks.

The $LD_{50}$ was calculated by the graphic method of J. T. Lichtfield and F. Wilcoxon (J. Pharm. Exp. Ther. 1949, 96: 99–133).

The $LD_{50}$ is comparable in both animals, and amounts to 1.30 g/kg both after 48 hours and after 14 days.

Acute toxicity was again determined in male mice by intravenous administration.

The $LD_{50}$ of the compound, as determined by intravenous administration, both after 3 minutes and after 14 days is 54.5 mg/kg with safety limits of $P = 0.05$ of 44.2 and 67.3 mg/kg.

Determination of Ocular Irritation

The method used is the method described in the Official Journal of Apr. 21, 1971, page 3863, and comprises applying to the right eye of each animal 0.1 ml of a 0.5% solution. The general total of the results is 0 which confirms the high tolerance of the product mentioned above.

Determination of aggressiveness to the skin by repeated application

The method used is the method described in the Official Journal of Apr. 28, 1971 for the analysis of cosmetics and beauty products, and comprises applying 0.5 cc of 2% solution over a period of 1 month to the two zones treated, one normal, the other raw, a control zone being reserved on the hindquarters of the animal.

Good local tolerance was observed in all the animals, and histological examination of pieces of skin taken from the animals did not reveal any significant modification. Haematological examination carried out on blood taken from the ear vein on completion of the test showed a normal blood formula.

Study of bacteriostatic activity

Compound 1, dissolved in distilled water, is introduced into a conventional gelose medium, pH 7 to 7.2, optionally containing 20% of horse serum.

The medium containing the solution to be tested is inoculated in the form of three single striae with a $10^{-5}$ times dilution of a bacterial culture aged 16 to 18 hours grown in salted peptone broth at a temperature of 37° C.

After inoculation, the media are stored at 37° C. for 48 hours, after which the bacterial growth is inspected. The MIC (minimum inhibiting concentrations) are expressed in micrograms of pure product per cubic centimeter of gelose medium required for inhibiting the culture ($\mu$g/cc). The control substance used is benzalconium chloride. The results obtained are shown in Table I below.

It is pointed out that the bacteriostatic activity of the product is particularly significant in the case of gram-negative bacteria, especially *Escherichia coli* and *Pseudomonas aeruginosa*.

TABLE I

| BACTERIA | WITHOUT SERUM | | WITH 20% OF SERUM | |
|---|---|---|---|---|
| | Compound 1 ($\mu$g/cc) | Control ($\mu$g/cc) | Compound 1 ($\mu$g/cc) | Control ($\mu$g/cc) |
| *Staphyloccus aureus* | 60 | 1.5 | 120 | 12 |
| *Bacillus subtilis* | 30 | 2.5 | 50 | 7.5 |
| *Escherichia coli* | 20 | 125 | 75 | 300 |
| *Pseudomonas aeruginosa* | 40 | 600 | 150 | 850 |
| *Pneumobacille* | 35 | 35 | 75 | 75 |
| *Serratia* | 20 | 10 | 75 | 30 |
| *Proteus vulgaris* | 40 | 35 | 150 | 75 |
| *Enterbacter cloacae* | 30 | 20 | 80 | 75 |
| *Moraxella glucidolytica* | 40 | 75 | 75 | 150 |

Determination of Bactericidal Activity

Bactericidal activity is determined by the following methods:

A titrate suspension of bacteria is brought into contact over a period of 2 hours at the temperature of the laboratory with increasing dilutions of the test product. The number of bacteria still alive are counted after passage through a filtering membrane. The results obtained are as follows:

TABLE II

| BACTERIA | MIC ($\mu$g/cc) |
| --- | --- |
| Escherichia coli | 50 |
| Pseudomonas aeruginosa | 50 |
| Bacillus subtilis | 50 |
| M pyogenes aureus | 100 |

An MIC study in a solid medium was carried out on 35 strains of *Bacillus pyocyaneus*, and showed that, for the majority of these strains, the minimum inhibiting concentration was 62.5 $\mu$g/cc.

Determination of the sporostatic activity (a) 1 cc of a suspension of spores of *B.subtilis* var. *Niger* containing approximately 200 spores is placed in one Petri dish, whilst 1 cc of a solution containing 3 g/100 cc of the product (mother solution) or of the same mother solution diluted to 1/10th, 1/100th, etc. up to 1/100,000th, are placed in other Petri dishes. Following the addition of a culture medium, the dishes are agitated, cooled and then placed in an oven. The number of colonies obtained are then determined. The results are set out in the following Table:

TABLE III

| NUMBER OF DILUTIONS TO 1/10 OF COMPOUND 1 | NUMBER OF COLONIES (average of 2 tests No > 200) |
| --- | --- |
| 0 | 0 |
| 1 | 0 |
| 2 | 18 |
| 3 | >200 |
| 4 | >200 |
| 5 | >200 |

(b) A porous membrane 0.45$\mu$ thick is placed aseptically in a sterile filter support, covered with 10 cc of sterile distilled water containing 1 cc of mother solution of the product, followed by the addition of 1 cc of a suspension of spores of *B. subtilis* var. *Niger* containing approximately 40 spores. These liquids are drawn through the membrane, after which the membrane is transferred aseptically to a culture medium and placed in an oven. The operation is recommenced using up to 5 rinses of the membrane per 10 cc of sterile distilled water. The number of colonies developing is then determined. The results obtained are set out in the following Table:

TABLE IV

| NUMBER OF RINSES OF THE MEMBRANE | NUMBER OF COLONIES No = 37 |
| --- | --- |
| 0 | 3 |
| 1 | 4 |
| 2 | 35 |
| 3 | 38 |
| 4 | 48 |
| 5 | 55 |

Taking into account the dilution by the gelose culture medium, it can be seen, especially from Table III, that 20 $\mu$g/cc of compound 1 still show sporostatic activity.

The sporocidal activity of compound 1 was also tested and found to be positive, especially at temperatures above 35° C. and at a pH around 7.

Tests were also carried out to determine the bacteriostatic activity of other compounds according to the invention by the method described above and in comparison with known substances, in particular with benzalconium chloride (compound T in the Tables).

TABLE V

Compound $R-X-CH_2-CH(OH)-CH_2NH_2,A$

| COMPOUND NO. | R | X | A | CONSTANTS |
| --- | --- | --- | --- | --- |
| 1 | $C_{10}H_{21}$ | O | HCl | |
| 2 | $C_{12}H_{25}$ | O | HCl | |
| 3 | $C_{10}H_{21}$ | O | HBr | M.p. 120° C. |
| 4 | $C_6H_{13}$ | $CH_2$ | HCl | |
| 5 | $C_{10}H_{21}$ | O | $Cl^-(N^+\begin{smallmatrix}CH_3\\-CH_3\\CH_3\end{smallmatrix})$ | M.p. 88° C. |
| 6 | $C_8H_{17}$ | O | HCl | M.p. 55° C. (soft) |
| 7 | $C_7H_{15}$ | $CH_2$ | " | M.p. 195° C. |
| 8 | $C_9H_{19}$ | $CH_2$ | " | M.p. 200° C. |
| 9 | $C_{14}H_{29}$ | O | " | M.p. 65° C. (soft) |
| 10 | $C_{18}H_{37}$ | O | " | indeterminate |
| 11 | $CH_3$ | O | " | M.p. 92° C. |
| 12 | $C_2H_5$ | O | " | M.p. 60° C. |
| 13 | $C_{10}H_{21}$ | O | AcOH | M.p. 63° C. |
| 14 | $C_{10}H_{21}$ | S | HCl | M.p. 270° C. |

TABLE VI

M.I.C. ($\mu$g/cc)

| | Bacteriostase without serum | | | | Bacteriostase containing 20% of serum | | | |
| --- | --- | --- | --- | --- | --- | --- | --- | --- |
| | S. aureus | B. subtilis | E. coli | Pseudom. aeruginosa | S. aureus | B. subtilis | E. coli | Pseudom. aeruginosa |
| T | 1.5 | 1 | 125 | 500 | 10 | 2.5 | 200 | 750 |
| 1 | 20 | 15 | 20 | 50 | 75 | 60 | 60 | 250 |
| 2 | 10 | 5 | 20 | 800 | 75 | 30 | 100 | 1200 |
| T | 1.5 | 1 | 125 | 500 | 10 | 2.5 | 200 | 750 |
| 1 | 20 | 15 | 20 | 50 | 75 | 60 | 60 | 250 |
| 3 | 30 | 25 | 30 | 100 | 75 | 50 | 60 | 250 |
| T | 1.5 | 1 | 125 | 600 | 10 | 2.5 | 250 | 750 |
| 1 | 20 | 15 | 25 | 60 | 70 | 50 | 60 | 250 |
| 4 | 70 | 20 | 125 | 400 | 150 | 75 | 200 | 500 |
| T | 1.5 | 2 | 150 | 500 | 10 | 4 | 300 | 750 |
| 1 | — | — | — | — | — | — | — | — |
| 5 | 25 | 25 | 125 | 600 | 50 | 40 | 200 | 750 |
| T | 1 | 1 | 125 | 500 | 10 | 2.5 | 250 | 850 |
| 1 | 30 | 15 | 40 | 75 | 65 | 40 | 80 | 200 |
| 6 | >150 | 150 | 150 | 300 | >250 | 200 | 300 | 500 |
| T | 1 | 1 | 125 | 700 | 5 | 2.5 | 250 | 1200 |
| 1 | 50 | 15 | 25 | 150 | 75 | 40 | 75 | 400 |
| 7 | 75 | 30 | 75 | 200 | 150 | 50 | 150 | 500 |
| T | 1 | 1 | 125 | 700 | 5 | 2.5 | 250 | 1200 |
| 1 | 50 | 15 | 25 | 150 | 75 | 40 | 75 | 400 |

TABLE VI-continued

| | M.I.C. (μg/cc) | | | | | | | |
|---|---|---|---|---|---|---|---|---|
| | Bacteriostase without serum | | | | Bacteriostase containing 20% of serum | | | |
| | S. aureus | B. subtilis | E. coli | Pseudom. aeruginosa | S. aureus | B. subtilis | E. coli | Pseudom. aeruginosa |
| 8 | 20 | 3 | 10 | >1000 | 40 | 30 | 75 | >1500 |
| T | 1.5 | 1.5 | 150 | 700 | 5 | 2.5 | 300 | 1000 |
| 1 | 40 | 15 | 40 | 100 | 75 | 40 | 100 | 350 |
| 9 | 10 | 7 | >500 | 1250 | 50 | 30 | >1000 | 2500 |
| T | 1.5 | 1.5 | 150 | 700 | 5 | 2.5 | 300 | 1000 |
| 1 | 40 | 15 | 40 | 100 | 75 | 40 | 100 | 350 |
| 10 | >300 | >300 | >500 | 1300 | >500 | >500 | >1000 | >2500 |
| T | 1.5 | 1.5 | 150 | 700 | 5 | 2.5 | 300 | 1000 |
| 1 | 40 | 15 | 40 | 100 | 75 | 40 | 100 | 350 |
| 11 | >300 | >300 | >500 | >1300 | >500 | >500 | >1000 | >2500 |
| T | 1.5 | 1.5 | 150 | 700 | 5 | 2.5 | 300 | 1000 |
| 1 | 40 | 15 | 40 | 100 | 75 | 40 | 100 | 350 |
| 12 | >300 | >300 | >500 | >1300 | >500 | >500 | >1000 | >2500 |
| T | 1.5 | 1.5 | 150 | 700 | 5 | 2.5 | 300 | 1000 |
| 1 | 40 | 15 | 40 | 100 | 75 | 40 | 100 | 350 |
| 13 | 40 | 20 | 50 | 150 | 80 | 40 | 250 | 400 |
| T | 1.5 | 1.5 | 150 | 700 | 5 | 2.5 | 300 | 1000 |
| 1 | 40 | 15 | 40 | 100 | 75 | 40 | 100 | 350 |
| 14 | 10 | 5 | 50 | 200 | 70 | 30 | 250 | 600 |

It is pointed out that the variations in the bacteriostatic activity of compounds 1 and T correspond to variations in the experimental conditions and also in the strains tested, and it is for this reason that the control compounds were retested at the same time as the test compound.

In vitro tests on the activity of the compound of Example 1 were also carried out so as to determine the activity of that compound on *Bacillus pyocyaneus*. The results of determining the minimum inhibiting concentration on 100 different strains are as follows:

25 μg/cc for 20 strains
50 μg/cc for 70 strains
100 μg/cc for 10 strains

On the other hand, tests on 6 different strains showed that the bactericidal concentration was very similar to the MIC.

The activity of the compound of Example 1 was also tested in vivo, in particular the compound was tested for its effect on *Bacillus pyocyaneus* in the following manner:

Rats are intravenously injected with 1 ml of a $10^8$ solution of *Ps. aeruginosa*. A 20 cm² cutaneous excision was then made in the animals.

30 minutes after the injection, the bacteria injected were detected in the vicinity of the wound by the replica method on a solid nutritive medium.

One group of rats was sprayed with the compound of Example 1 (aqueous solution) in the vicinity of the wounds (1 to 3 times daily).

A group of control rats were sprayed with sterile distilled water.

In the treated rats, it was observed that 75% of the replica cultures were totally negative, and the positive cultures showed only a very small number of colonies in relation to the control rats.

Local tolerance was good, and the healing process was normal.

Accordingly, the compound of Example 1 would appear to be effective to a certain extent in controlling the infection of excised wounds in rats infected with *Ps. aeruginosa*.

Accordingly, the above tests clearly demonstrate the excellent activity of this compound according to the present invention, in particular with respect to gram-negative bacteria.

What is claimed is:

1. A method of sterilizing instruments or apparatus and of antisepticizing humans and animals against gram negative bacteria comprising applying thereto, an effective amount of the compound of the formula $$R-X-CH_2-CH(OH)-CH_2NH_2 \qquad \text{(Formula I)}$$

wherein R represents a saturated or unsaturated straight chain $C_5$ to $C_{18}$ aliphatic radical, and X represents O or S or the salts of these compounds.

2. The method of claim 1 wherein $R_1$ is $C_5$-$C_{14}$ alkyl radical.

3. The method of claim 1 wherein the compound is in the form of a hydrochloride or hydrobromide salt.

4. The method of claim 2 wherein the compound is in the form of a hydrochloride or a hydrobromide salt.

5. The process of claim 1 wherein the compound of Formula I is 3-decyloxy-2-hydroxy-1-aminopropane hydrochloride, 3-decylthio-2-hydroxy-1-aminopropane hydrochloride, 3-decyloxy-2-hydroxy-1-aminopropane acetate, 3-decyloxy-2-hydroxy-1-aminopropane hydrobromide, or 3-dodecyl-2-hydroxy-1-aminopropane hydrochloride.

* * * * *